(12) United States Patent
Suijs

(10) Patent No.: US 9,775,960 B2
(45) Date of Patent: Oct. 3, 2017

(54) ENDOTRACHEAL TUBE FOR MECHANICAL VENTILATION

(75) Inventor: Emiel Suijs, Asse (BE)

(73) Assignee: VRIJE UNIVERSITEIT BRUSSEL, Brussels (BE)

( * ) Notice: Subject to any disclaimer, the term of this patent is extended or adjusted under 35 U.S.C. 154(b) by 507 days.

(21) Appl. No.: 13/821,189

(22) PCT Filed: Sep. 12, 2011

(86) PCT No.: PCT/EP2011/065743
§ 371 (c)(1),
(2), (4) Date: Mar. 6, 2013

(87) PCT Pub. No.: WO2012/032186
PCT Pub. Date: Mar. 15, 2012

(65) Prior Publication Data
US 2013/0160771 A1 Jun. 27, 2013
US 2014/0000623 A9 Jan. 2, 2014

Related U.S. Application Data

(60) Provisional application No. 61/381,792, filed on Sep. 10, 2010.

(30) Foreign Application Priority Data

Sep. 10, 2010 (GB) .................................. 1015078.7

(51) Int. Cl.
*A61M 16/00* (2006.01)
*A61M 16/04* (2006.01)

(52) U.S. Cl.
CPC .............................. *A61M 16/0434* (2013.01)

(58) Field of Classification Search
CPC .......... A61M 16/0486; A61M 16/0434; A61M 16/04; A61M 16/0459; A61M 16/0479; A61M 16/044
See application file for complete search history.

(56) References Cited

U.S. PATENT DOCUMENTS 4,233,984 A * 11/1980 Walling ................ A61M 16/04
128/207.14
4,235,239 A * 11/1980 Elam ........................ 128/207.15
4,423,725 A * 1/1984 Baran et al. .............. 128/207.15
5,315,992 A 5/1994 Dalton
5,765,559 A 6/1998 Kim
(Continued)

FOREIGN PATENT DOCUMENTS

EP 0596517 A1 5/1994
WO WO 2008/074468 A1 6/2008

OTHER PUBLICATIONS

International Search Report for International Application No. PCT/EP2011/065743, mailed on Nov. 30, 2011.

*Primary Examiner* — Bradley Philips
*Assistant Examiner* — Victoria Murphy
(74) *Attorney, Agent, or Firm* — Knobbe, Martens, Olson & Bear LLP

(57) ABSTRACT

The present invention relates generally to medical devices, methods, and kits. More particularly, the present invention relates to improved endotracheal tubes or patient ventilation tubes which prevent the leakage of proximal secretions to the distal airways.

14 Claims, 5 Drawing Sheets

(56) References Cited

U.S. PATENT DOCUMENTS

| | | | |
|---|---|---|---|
| 7,204,252 B2* | 4/2007 | Johnson | A61M 16/04 128/207.14 |
| 2002/0014238 A1 | 2/2002 | Kotmel | |
| 2009/0260632 A1 | 10/2009 | Abnousi et al. | |

* cited by examiner

ENDOTRACHEAL TUBE FOR
MECHANICAL VENTILATION

CROSS-REFERENCE TO RELATED
APPLICATIONS

This application is the U.S. National Phase under 35 U.S.C. §371 of International Application PCT/EP2011/065743, filed Sep. 12, 2011, which claims priority to U.S. Provisional Application No. 61/381,792, filed Sep. 10, 2010 and GB 1015078.7, filed Sep. 10, 2010.

FIELD OF THE INVENTION

The present invention relates generally to medical devices, methods, and kits. More particularly, the present invention relates to improved endotracheal tubes or patient ventilation tubes which prevent the leakage of proximal secretions to the distal airways.

BACKGROUND OF THE INVENTION

Mechanical ventilation by placement of endotracheal and other ventilation tubes can be a necessity for patients for a variety of reasons. For example, patients receiving anesthetics may require ventilation to temporarily take over their natural breathing mechanism. Here mechanical ventilation is used only for a relatively short period of time. Patients suffering from respiratory failure, in contrast, may be intubated and ventilated for days, weeks, or even longer while in intensive care. Ventilation tubes which enter the trachea through a patient's mouth or nose are generally referred to as endotracheal tubes. Ventilation tubes which are inserted through an incision in the neck are usually referred to as tracheostomy tubes. In both cases, the devices will include a ventilation tube having a central lumen to provide for ventilation of the patient.

Ventilator-associated pneumonia (VAP) is an infection which occurs especially in patients who are on mechanical ventilation through an endotracheal or tracheostomy tube for a considerable amount of time. VAP is a medical condition that results from infection which floods the alveoli, the small, air-filled sacs in the lung responsible for absorbing oxygen from the atmosphere. It is known to be caused by the leakage of proximal fluids during intubation into the distal airways. VAP is distinguished from other kinds of infectious pneumonia by the different types of microorganisms responsible, the antibiotics used in treatment, the methods of diagnosis and the effective preventive measures. While community-acquired pneumonia is most often caused by *S. pneumoniae*, *H. influenzae*, or *S. aureus*, the organisms associated with VAP are most often Gram-negative bacteria, such as *Pseudomonas aeruginosa*.

The occurrence of VAP leads to increased duration of ventilation and ICU stay and is associated with a high attributable mortality. VAP also leads to more and specific antibiotic use, increasing the risk of development of multi-drug resistant bacteria.

A wide array of VAP prevention measures has already been undertaken. Generally, these measures consist of positional, physical and pharmacological interventions. In general these measures involve limiting exposure of the patient to resistant bacteria, discontinuing mechanical ventilation as soon as possible, and a variety of strategies to limit infection while the patient is intubated. Resistant bacteria are spread in much the same ways as any communicable disease. Proper hand washing, sterile technique for invasive procedures, and isolation of individuals with known resistant organisms are all mandatory for effective infection control.

Other recommendations for preventing VAP include raising the head of the bed to at least 30 degrees and placement of feeding tubes beyond the pylorus of the stomach. Antiseptic mouth washes such as chlorhexidine may also reduce the incidence of VAP.

The endotracheal or tracheostomy tube is a critical device in mechanical ventilation, as it is the tube connecting the patient to the ventilator, through which air is driven into the lungs. Following insertion of the tube into the trachea, a balloon (or cuff) around the tube is inflated, typically up to a maximum pressure of 30 cm $H_2O$, which allows fixation of the tube. The cuff also prevents inflow of proximal secretions to the distal airways. As these secretions can be bacteriologically contaminated, the leakage of these secretions is considered to be one of the most important causes of VAP. Due to the presence of the cuff, these secretions will accumulate above the cuff. Adaptations to endotracheal or tracheostomy tubes to prevent leakage of secretions in the lungs and/or to "disinfect" the tube internally have been proposed, such as supraglottic secretion drainage (SSG), double-cuffed tubes, continuous or intermittent subglottic drainage, tubes with a polyurethane cuff (e.g. Kimberly-Clark Microcuff® endotracheal tubes) and silver-coated endotracheal or tracheostomy tubes (e.g. Agento® I.C. silver-coated endotracheal tube).

In spite of the use of these new types of endotracheal or tracheostomy tubes, the leakage of the proximal secretions to the distal airways still occurs. Consequently VAP is still diagnosed on a frequent basis.

Accordingly, there is a need for improved endotracheal or tracheostomy tubes or patient ventilation tubes which prevent the leakage of proximal secretions to the distal airways.

SUMMARY OF THE INVENTION

The present invention provides improved ventilation devices, ventilation device kits, and methods for ventilating patients. The present invention specifically relates to improved ventilation tubes which prevent the leakage of proximal secretions to the distal airways. Whereas in double-cuffed ventilation tubes, proximal secretions typically accumulate above the proximal positioned cuff or primary cuff and the distal positioned cuff or secondary cuff is typically used as a secondary seal, the present invention provides devices and methods which provide a positive pressure in the region between the primary and secondary cuff, thereby avoiding leakage of the secretions into the inter-cuff chamber.

In conventional double-cuffed systems the barriers to prevent leakage are physical barriers (the cuffs) that nevertheless show leakages, regardless the material the cuffs are made of. The inventor has now found that pressurization of the chamber formed by the ventilation tube, the primary and secondary cuff and the wall of the trachea seems to be essential for avoiding that proximal secretions reach the distal airways. The positive pressure in the inter-cuff chamber seems to form a barrier that reduces further leakage to a minimum. The inventor therefore proposes a double-cuffed ventilation device which further comprises means for providing a continuous positive pressure in said inter-cuff chamber. The pressurization of said inter-cuff chamber is established by providing the ventilation tube according to the present invention with a pressurization lumen for pressurizing said inter-cuff region, said pressurization lumen having an external port near the proximal end of said ventilation tube and an internal port positioned between said primary and secondary cuff. Said pressurization lumen may be connected to a pressure regulator that continuously measures and adapts pressure in the inter-cuff chamber.

The inventor has found that the continuous positive pressure in the inter-cuff chamber generates an upward air flow which "pushes" secretions that tend to leak alongside the proximal cuff into the direction of the oropharynx where they can remain or can be aspirated easily.

In a first aspect the invention provides a ventilation device for mechanical ventilation suitable to be partly positioned inside the trachea of a patient, comprising:

a ventilation tube having a proximal end, preferably suitable to be constrained to a machine or apparatus for mechanical ventilation and a distal end;

a primary cuff, preferably suitable to allow sealing of said device inside the trachea, and a secondary cuff in distal position with respect to said primary cuff, said primary and secondary cuffs being provided with one or more cuff inflation lumens, suitable to inflate and/or deflate said primary and/or secondary cuffs; and;

an inter-cuff region positioned between said primary cuff and said secondary cuff, in distal position with respect to said primary cuff and in proximal position with respect to said secondary cuff;

characterized in that said ventilation device additionally comprises a pressurization lumen for pressurizing said inter-cuff region, said pressurization lumen having an external port near the proximal end of said ventilation tube and an internal port positioned between said primary and secondary cuff or on said inter-cuff region.

In yet another embodiment the present invention relates to a ventilation system comprising:

(a) a ventilation device according to the present invention;
(b) a ventilation source connected to said proximal end of said ventilation tube;
(c) an inflation device suitable for selectively inflating and/or deflating said primary and secondary cuffs, said inflation device being connected to said one or more cuff inflation lumens; and
(d) a pressure regulator connected to said pressurization lumen which selectively pressurizes or depressurizes said inter-cuff region between said primary and said secondary cuff.

In yet another embodiment, the present invention relates to a method for ventilating a patient comprising the steps of:

providing a ventilation device according to the present invention;
inserting said ventilation device orally into a patient;
inflating said primary and secondary cuff;
pneumatically pressurizing the inter-cuff chamber formed by the trachea wall, the inter-cuff region and the primary and secondary cuffs such that the pressure inside said inter-cuff chamber is larger than the pressure proximal from said primary cuff;
delivering oxygen to said patient through said ventilation tube.

In yet another embodiment, the present invention relates to a kit comprising a ventilation device according to the present invention or a ventilation system according to the present invention and instructions for use setting forth the method according to the present invention.

Figure 1:
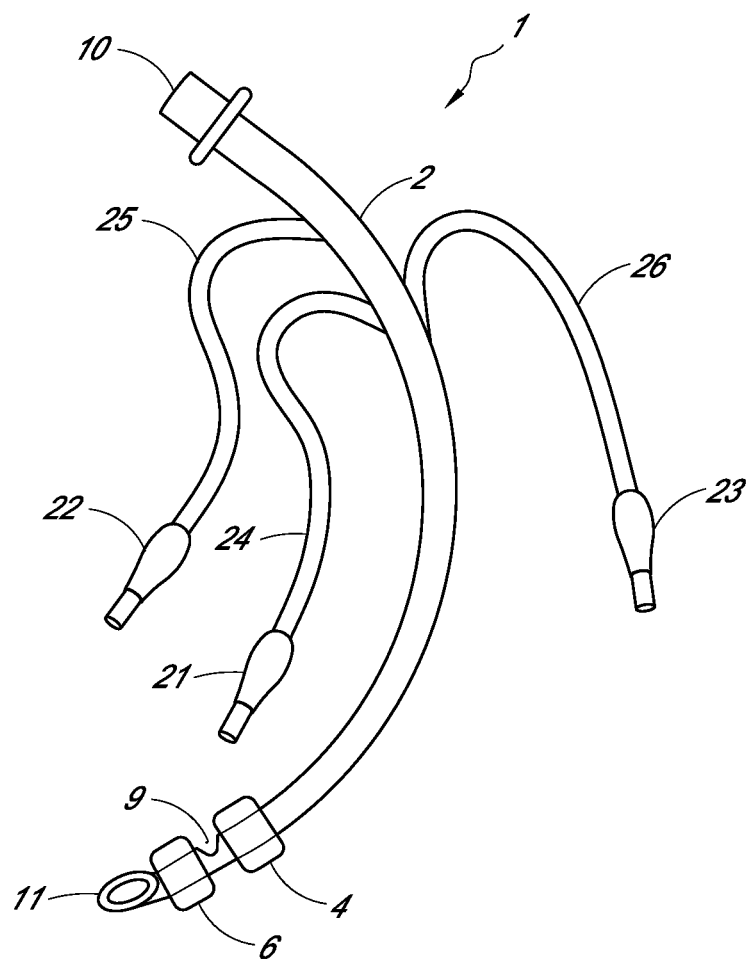
FIG. 1 illustrates an exemplary embodiment of a ventilation device according to a particular embodiment of the invention.

Each of these illustrations represents particular embodiments of the features concerned and the corresponding features are not to be interpreted as limited to this specific embodiment.

DETAILED DESCRIPTION OF THE INVENTION

The terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. As used herein embodiments where the terms "comprising", "comprises" and/or "comprised of" are used alternatively also provide that these embodiments may be provided with the wording "consisting of".

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

All documents cited in the present specification are hereby incorporated by reference in their entirety.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

The present invention provides improved ventilation devices, ventilation device kits, and methods for ventilating patients. The present invention specifically relates to improved ventilation tubes which prevent the leakage of proximal secretions to the distal airways. Whereas in double-cuffed ventilation tubes proximal secretions typically accumulate above the proximal positioned cuff or primary cuff and the distal positioned cuff or secondary cuff is typically used as a secondary seal, the present invention provides devices and methods which provide a positive pressure in the region between the primary and secondary cuff, thereby avoiding leakage of the secretions into the inter-cuff chamber.

In conventional double-cuffed systems the barriers to prevent leakage are physical barriers (the cuffs) that nevertheless show leakages, even despite high cuff pressures and the material the cuffs are made of. The inventor has now found that pressurization of the chamber formed by the ventilation tube, the primary and secondary cuff and the wall of the trachea seems to be essential for avoiding that proximal secretions reach the distal airways. The positive pressure in the inter-cuff chamber seems to form a barrier that reduces further leakage to a minimum. The inventor therefore proposes a double-cuffed ventilation device which further comprises means for providing a continuous positive pressure in said inter-cuff chamber. The pressurization of said inter-cuff chamber is established by providing the ventilation tube according to the present invention with a pressurization lumen for pressurizing said inter-cuff region, said pressurization lumen having an external port near the proximal end of said ventilation tube and an internal port positioned between said primary and secondary cuff. Said pressurization lumen may be connected to a pressure regulator that continuously measures and adapts pressure in the inter-cuff chamber.

The inventor has found that the continuous positive pressure in the inter-cuff chamber generates an upward air flow which "pushes" secretions that tend to leak alongside the proximal cuff into the direction of the oropharynx where they can remain or can be aspirated easily.

In a first aspect the invention provides a ventilation device for mechanical ventilation suitable to be partly positioned inside the trachea of a patient, comprising:

a ventilation tube having a proximal end, preferably suitable to be constrained to a machine or apparatus for mechanical ventilation and a distal end;

a primary cuff, preferably suitable to allow sealing of said device inside the trachea, and a secondary cuff in distal position with respect to said primary cuff, said primary and secondary cuffs being provided with one or more cuff inflation lumens, suitable to inflate and/or deflate said primary and/or secondary cuffs; and;

an inter-cuff region positioned between said primary cuff and said secondary cuff, in distal position with respect to said primary cuff and in proximal position with respect to said secondary cuff;

characterized in that said ventilation device additionally comprises a pressurization lumen for pressurizing said inter-cuff region, said pressurization lumen having an external port near the proximal end of said ventilation tube and an internal port positioned between said primary and secondary cuff or on said inter-cuff region.

As used herein the term "ventilation device" refers to any type of device suitable for the ventilation of a patient and to be partly positioned inside the trachea of said patient. Said ventilation device may for instance refer to an endotracheal or tracheostomy tube. In general said ventilation device refers to a flexible plastic catheter to be placed into the trachea of a patient to protect the airway and provide a means of mechanical ventilation.

The ventilation devices according to the present invention comprise a ventilation tube having a proximal end and a distal end. The distal end is adapted to be positioned in the trachea of a patient to deliver air in order to mechanically ventilate the patient (and optionally deliver anesthetics or other bioactive agents) in a conventional manner. The proximal end will be adapted to be connected to a conventional mechanical ventilation system or apparatus. The ventilation tube will typically have a length in the range from about 15 cm to 35 cm, an outside range diameter from 4 mm to 15 mm (although in certain embodiments the ventilation tube of the present invention will have a non-circular cross-section), and a ventilation lumen having a diameter in the range from 2.5 mm to 10 mm.

The ventilation devices according to the present invention further comprise at least two inflatable cuffs. A primary cuff is disposed on the ventilation tube and a secondary cuff is located distally of the primary cuff. The secondary cuff is preferably positioned near the distal end of the ventilation tube.

The primary and secondary cuffs may be inflated from a collapsed or low profile configuration to an expanded or inflated configuration. The construction, dimensions, and other aspects of the primary cuff are commonly known. The secondary cuff, which is spaced distally of the primary cuff is also inflatable and typically has dimensions generally the same of those of the primary cuff. In certain embodiments, both cuffs have the same length.

In other embodiments the cuffs differ in length. Indeed, the inventor has found that devices according to the present invention having a primary cuff which is shorter than the secondary cuff provide further advantages. Specifically, the length of the primary cuff may be reduced to increase the air flow from the inter-cuff chamber in the direction of the oropharynx, whereas the length of the secondary should be sufficient to adequately prevent the inflow of proximal secretions to the distal airways. Furthermore, in particular cases, e.g. where the length of the trachea is limited, it may be of interest to reduce the length of the proximal cuff, while maintaining the standard length of the distal cuff. Accordingly, in a particular embodiment, the present invention relates to a ventilation device according to the present invention, wherein said primary cuff has a length in axial direction of said ventilation tube which is shorter compared to the length of said secondary cuff.

Typical cuff lengths vary between 0.5 and 4 cm, more particularly between about 2 and about 3 cm. In particular embodiments of the present invention, the primary cuff has a length of approximately between 0.5 cm and 4 cm, more particularly between 0.5 and 3 cm, preferably about 2 cm. In particular embodiments, the secondary cuff is at least 1 mm, 3 mm, 5 mm, 7 mm or 10 mm longer in axial direction of the ventilation tube than the primary cuff. Thus, in a particular embodiment, the primary cuff has a length of about 20 mm, and the secondary cuff has a length of about 25 mm. While the diameter of the cuffs is as such not critical to the present invention, they of course have an impact on the sealing properties of the cuffs and thus the functioning of the device. Typically it is envisaged that the cuff resting diameter is between 20-35 mm, preferably between 25-35 mm, more preferably about 30 mm. The cuff diameter is determined by the diameter of the trachea and, most particularly for the secondary cuff, it is important that it does not allow passage of fluid. Typically, the proximal and the distal cuff have the same cuff resting diameter. However, in some cases the cuff resting diameter of the proximal cuff may be slightly smaller than the cuff resting diameter of the distal cuff, this may facilitate the air flow from the inter-cuff chamber into the direction of the oropharynx. Accordingly, in particular embodiments, the cuff resting diameter of the proximal cuff is at least 1 mm, 2 mm or 3 mm smaller than the cuff resting diameter of the distal cuff.

While an inflatable primary and secondary cuff are illustrated, it will be appreciated that the present invention could also employ other deployable isolation barriers, such as collars, rings, flanges, or other barriers that can be opened radially outward to seal against the inner surface of the trachea after the ventilation device has been deployed in a patient's trachea.

According to particular embodiments, the cuffs are inflatable cuffs. In general, tracheal tubes comprise ducts, called lumens which place said cuff in communication with an external valve. More particularly said cuff inflation lumens extend along the wall of the ventilation tube between said cuff and the proximal end of said ventilation tube.

Suitable materials for the primary and secondary cuff of the devices of the present invention are known in the art and this aspect is not critical to the invention. In particular embodiments, however, the cuffs are provided in PVC or a similar material. The selection of material may influence the occurrence of a backflow of air during the inspiratory and at least part of the expiratory phase when the device is in use, such that "humidified" air enters the inter-cuff region and mixes with the air flow provided by the pressurization lumen. This will cause condensation in the inter-cuff region which is of interest to protect against dryness or trauma. In further particular embodiments, the cuffs are provided in polyurethane (PU).

Said primary and secondary cuffs are thus connected to one or more cuff inflation lumens that allow the inflation and/or deflation of said primary and/or secondary cuffs. Said cuff inflation lumen(s) permit of inflation of the cuffs when the ventilation device is deployed. In particular embodiments, the primary and secondary cuffs share a single cuff inflation lumen. This implies that the pressure in the cuffs is regulated in the same way for both the primary and the secondary cuff.

The inventor has however noted that devices according to the present invention wherein the primary and secondary cuff are provided with a separate inflation lumen, provide further advantages. Thus, in specific embodiments, the primary cuff and the secondary cuff are each provided with a dedicated cuff inflation lumen. This allows to obtain a different pressure in the primary and secondary cuffs. For example, a lower pressure in the primary cuff than in the pressure in the secondary cuff ensures a flow from the inter-cuff chamber into the direction of the oropharynx. This can be of interest when extubating, as will be detailed below.

Cuff inflation lumens may comprise separate tubes attached to the exterior of the ventilation tube, but may also comprise in whole or in part lumens formed within the wall of the ventilation tube.

The primary and secondary cuffs are typically inflated to a pressure variable as a function of the patient and on average of between 20 cm $H_2O$ and 30 cm $H_2O$ (centimeters of water, 1 cm $H_2O$ is equal to 98.0638 Pascal).

The part of the ventilation tube between the primary cuff and the secondary cuff, and more particularly the part of the ventilation tube in distal position with respect to said primary cuff and in proximal position with respect to said secondary cuff is referred to as the inter-cuff region of the ventilation tube.

The position of the ventilation tube in the trachea ranges from the vocal cords to the bifurcation. This is a length of about 10 cm. Within this length both cuffs must be inflated. This allows an inter-cuff (if fully inflated) space of ranging between 0.5 and 3 cm. Accordingly in particular embodiments, the present invention relates to a ventilation device according to the present invention, wherein said primary and said secondary cuff are axially spaced apart by a distance between 0.5 cm and 3 cm, preferably between 0.5 cm and 2 cm, for example about 1 cm.

As indicated hereabove, both cuffs must be inflated within a length of about 10 cm, in some cases even less. Accordingly, in particular embodiments, the total length of both cuffs, the inter-cuff chamber and the distal end of the ventilation tube beyond the secondary cuff is below 9 cm, preferably below 8 cm, for example about 7 cm.

Of particular interest to the present invention is that a pressurization lumen is provided in the wall of the ventilation tube and terminates in an external connector at the proximal end of the ventilation device which ensures pressurization of the inter-cuff region. More particularly the pressurization lumen terminates at a port disposed between the primary cuff and the secondary cuff. In this way, air can be introduced through the pressurization lumen connector and into the isolated region between the two cuffs. More particularly said pressurization lumen extends along the wall of the ventilation tube between said inter-cuff region and the proximal end of said ventilation tube. The pressurization lumen may comprise a separate tube attached to the exterior of the ventilation tube, but can also comprise in whole or in part lumens formed in the wall of the ventilation tube.

The pressurization lumen is a dedicated pneumatic lumen provided with a connection element for applying a positive pressure in the inter-cuff chamber i.e. the chamber formed by the ventilation tube, the primary and secondary cuff and the wall of the trachea. The pressurization lumen has been found to be essential for avoiding that proximal secretions reach the distal airways.

Typically, the pressurization lumen has an inside diameter between 4 mm and 1 mm, particularly between 3.5 mm and 1 mm, more particularly between 3 mm and 1.5 mm, and even more particularly between 2.5 mm and 1.5 mm, such as about 2 mm. In further embodiments the pressurization lumen has an inside diameter of less than 2.5 mm, more particularly of 1.5 mm or smaller. The small diameter of the pressurization lumen is possible as the pressure drop over the lumen is limited due to the use of gas or air. Such small diameters can not be used in fluidic tubing as the pressure drop over the lumen would be too large and require a pressurization of more than 10 bar. It can be envisaged that the inside diameter of the pressurization lumen is smaller than 1.5 mm, smaller than 1.4 mm, smaller than 1.3 mm, smaller than 1.2 mm, smaller than 1.1 mm and even smaller than 1 mm, however, higher pressure will need to be applied at the source to ensure the same inter-cuff pressure.

The obtainable gas flow through the pressurization lumen is influenced by the length and the diameter of the lumen: an increased lumen diameter and/or a decreased lumen length increases the obtainable flow. However, the maximal diameter of the pressurization lumen is governed by the limited space available in the ventilation device and the trachea, particularly when the pressurization lumen is formed in the wall of the ventilation tube. For the portion of the pressurization lumen that is extends proximally outside the ventilation tube, the diameter is not subject to this constraint.

Accordingly, in certain embodiments, the pressurization lumen comprises two or more regions with a different diameter. The diameter of the region within the ventilation tube is typically as described herein above. In particular embodiments, the diameter of the pressurization lumen increases in discrete sections extending proximally from the ventilation tube. For example, the diameter of the pressurization lumen can be 2.5 mm within the ventilation tube, extend to 3 mm in the section directly above the ventilation tube, and further increase to 4 mm in a section connecting the ventilation lumen to a pressurization device.

By applying a positive pressure inside said inter-cuff chamber, leakage of secretions alongside the primary cuff is avoided leading to a reduction and even a zero incidence of VAP caused by leakage of secretions. The ventilation device according to the present invention is furthermore more economical compared to other types of ventilation devices such as for instance silver-coated ventilation tubes, which are highly expensive. Furthermore, by reducing the incidence of VAP antibiotic prophylaxis is avoided as well.

In a particular embodiment, the present invention relates to a ventilation device according to the present invention, wherein said pressurization lumen is provided with a connection element, more particularly a dedicated connection element, for connection of the pressurization lumen to a pressure regulator. In particular embodiments, the connection element is a luer lock, a luer slip or the like. In certain embodiments, the connection element is an external pneumatic valve, more particularly a two-way valve.

More particularly, the pressurization lumen is a dedicated pneumatic lumen provided with a connection element for connecting said lumen to a pressure regulator which is adapted for discharging pressurized gas into the pneumatic lumen. The pressure regulator refers to a regulator, known in the art, which automatically cuts off the flow of a gas at a predetermined pressure. Accordingly the pressure regulator provides a continuous inflow of gas into the pressurization lumen and the inter-cuff chamber, thereby maintaining the positive pressure in the inter-cuff chamber at a constant value.

The pressure regulator as used in the present invention refers to an external device that provides a sufficient gas flow for generating a positive pressure in the inter-cuff chamber and to constantly monitor and adapt the pressure in said inter-cuff chamber.

The application of a positive pressure in said inter-cuff chamber furthermore provides a continuous flow of the secretions into the direction of the oropharynx where they can remain or can be aspirated easily. It is also often seen in known ventilation devices that the pressure of the cuffs is elevated in order to reduce the amount of leakage. However, it has been seen that inflation of the cuffs at high pressures, up to 30 cm $H_2O$, lead to problems of the trachea as the blood flow trough the trachea wall is reduced due to the high pressures of the cuffs. In the ventilation device according to the present invention it is not required that the cuffs are inflated at such high pressures as the positive pressure in the inter-cuff chamber provides a barrier that is not penetrable by the proximal secretions. The positive pressure in the inter-cuff chamber will furthermore compensate for the progressive loss of the cuff pressure, which occurs over time in all ventilated patients, and which causes the leakage of secretions alongside the cuffs. Moreover, the ventilation device according to the present invention further allows that the cuffs need not to be inflated at high pressures, avoiding tracheal trauma and late stricture lesions. This is further demonstrated in example a).

Also, it has been seen that the ventilation device according to particular embodiments of the present invention is in addition beneficial when disconnecting the patient from the ventilator. Disconnection results in an abrupt fall of Positive End-Expiratory Pressure (PEEP, see further) to 0 (zero) cm $H_2O$, which significantly increases the risk of leakage of proximal secretions to the distal airways. However, in the ventilation device according to the present invention, the positive inter-cuff pressure prevents such leakage. This is further demonstrated in example b).

Furthermore, the ventilation device according to particular embodiments of the present invention is beneficial when removing the ventilation device from the trachea of the patient. Typically, removal of the ventilation device from the trachea is a very delicate process that not only requires a reduction of the pressure of the cuffs but also results in an abrupt fall of PEEP. The combination of these events significantly increases the risk of leakage of proximal secretions to the distal airways. However, the connection to a pneumatic pressure regulator in the ventilation device according to the present invention prevents leakage of the secretions upon removal of the ventilation device from the trachea of the patient. Indeed, in particular embodiments, the removal of the ventilation device according to the present invention from the trachea involves the reduction of pressure in the proximal cuff, while maintaining the pressure in the distal cuff and maintaining or increasing the air flow in the pressurization lumen. The air flow then causes movement of any fluid accumulated above the proximal cuff in the proximal direction of the trachea, where it can be removed easily. Afterwards, the device can be removed from the trachea of the patient.

As used herein the term "positive pressure" particularly refers to a (pneumatic) pressure of at least 2.5 cm $H_2O$, more particularly at least 3 cm $H_2O$, more particularly at least 3.5 cm $H_2O$, more particularly at least 4 cm $H_2O$, more particularly at least 4.5 cm $H_2O$ and most particularly at least 5 cm $H_2O$. In particular embodiments the positive pressure is 5 cm $H_2O$. In further embodiments the positive pressure is at least 6 cm $H_2O$, 7 cm $H_2O$, 8 cm $H_2O$, 9 cm $H_2O$, 10 cm $H_2O$, 11 cm $H_2O$ or 12 cm $H_2O$. A person skilled in the art will appreciate that the positive pressure in the inter-cuff chamber preferably does not exceed the applied Positive End-Expiratory Pressure (PEEP). However, in some cases, the positive pressure in the inter-cuff chamber may be up to 1 cm $H_2O$ higher than the applied PEEP, particularly when the pressure in the primary cuff is lower than the pressure in the secondary cuff.

PEEP is a term used in mechanical ventilation to denote the amount of pressure above atmospheric pressure present in the airway at the end of the expiratory cycle. By setting that the positive pressure in the inter-cuff chamber does not exceed the applied PEEP, the secondary cuff remains secured and sealed for any secretions arriving at its level by the positive pressure ventilation used to ventilate the patient.

In a particular embodiment, the present invention relates to a ventilation device according to the present invention, wherein at least three internal ports of said pressurization lumen are provided on said inter-cuff region, said internal ports being positioned symmetrically along a single circumferential sector of said tube.

In particular, by providing by distributing the internal ports of said pressurization lumen symmetrically along a single circumferential sector of the ventilation tube, the discharge of the gas flow inside the inter-cuff chamber is distributed evenly.

In particular treatments it may be of interest to be able to administer a (therapeutic) substance to the respiratory system of the patient, while the ventilation device is maintained in position. Thus, it is envisaged, that in particular embodiments, the ventilation devices according to the present invention, in addition to the features described herein further comprise a lumen having an external port near the proximal end of said ventilation tube and an internal port near the distal end of said ventilation tube, said lumen being suitable to allow inoculation of substances directly into the respiratory system of the patient.

The devices of the present invention significantly reduce the leakage of proximal fluids during intubation, observed with prior art ventilation devices. However, in particular embodiments it can be envisaged that the features of the present invention are combined with prior art systems to further reduce the accumulation of proximal fluids in/around the ventilation device.

Accordingly, in a particular embodiment, the ventilation device according to the present invention, may, in addition to (and separate from) the pressurization lumen envisaged herein further be provided with one or more aspirating and/or irrigating lumens.

Additionally or alternatively, in particular embodiments, the ventilation device may further comprise one or more aspiration lumens provided on or along the ventilation tube, said aspiration lumens comprising an external port near the proximal end of the ventilation tube and an internal port preferably proximal of the primary cuff as proximal secretions will accumulate there and can be aspirated at that location. The aspiration lumen permits aspiration of the secretions above the cuffs. The aspiration lumen may also be used to introduce irrigant to facilitate washing of the region, but often one or more additional irrigation lumen(s) will be provided on or in the ventilation tube so that irrigation and aspiration of the isolated region is facilitated.

In a particular embodiment, the present invention relates to a ventilation device according to the present invention, wherein said ventilation device is an endotracheal or tracheostomy device.

In yet a further aspect the present invention relates to a ventilation system comprising:
 (a) a ventilation device according to the present invention; and one or more of the following:
 (b) a ventilation source connected to said proximal end of said ventilation tube;
 (c) an inflation device suitable for selectively inflating and/or deflating said primary and secondary cuffs, said inflation device being connected to said one or more cuff inflation lumens; and
 (d) a pressure regulator connected to said pressurization lumen which selectively pressurizes of depressurizes said inter-cuff region between said primary and said secondary cuff.

The ventilation devices according to the present invention may be incorporated into ventilation systems which facilitate deployment and management of the ventilation device. Such ventilation systems typically comprise a ventilation device according to the present invention; in addition such systems may comprise one or more of the following:
 a ventilation source for mechanical ventilation, which delivers air to and expel air from the human body through the ventilation tube, so as to implement mechanical ventilation;
 an inflation device suitable for selectively inflating and/or deflating said primary and secondary cuffs and a pressure regulator connected to said pressurization lumen which selectively pressurizes of depressurizes said inter-cuff region between said primary and said secondary cuff.

Particularly said ventilation system may further comprise a controller. Said controller may be a digital controller, a computer, an electromechanical programmable controller, or any other control system of a type capable of operating valves, solenoids, timers, making pressure measurements, and the like. The controller of the present invention will selectively control the inflation and deflation of the cuffs. The controller will also control the pressurization and depressurization of the inter-cuff chamber.

In a particular embodiment, the present invention relates to a ventilation system according to the present invention, wherein said pressure regulator controls delivery of air to said inter-cuff region.

In a particular embodiment, the present invention relates to a ventilation system according to the present invention, wherein said pressure regulator operates on a continuous basis.

A further aspect of the present invention relates to the devices and systems described herein, for ventilating a patient in need thereof. More particularly, the use of the devices and systems of the present invention is envisaged for ventilating patients in need thereof which use involves pressurizing the region formed between the cuffs. Accordingly in a particular embodiment, the present invention relates to methods for ventilating a patient in need thereof comprising the steps of:
 providing a ventilation device according to the present invention;
 inserting said ventilation device orally into a patient;
 inflating said primary and secondary cuff; and more particularly inflating the proximal cuff and than inflating the distal cuff;
 pressurizing the inter-cuff chamber formed by the trachea wall, the inter-cuff region and the primary and secondary cuffs.
 delivering oxygen to said patient through said ventilation tube.

More particularly, when pressurizing the inter-cuff chamber, the pressure inside said chamber remains higher than the pressure proximal from said primary cuff. The pressure proximal from said primary cuff normally equals 0 (zero) cm $H_2O$ but could become slightly higher in case secretions are accumulating.

In certain embodiments, the pressure in the primary cuff is at least 1 cm $H_2O$, 3 cm $H_2O$ or 5 cm $H_2O$ lower than the pressure in the secondary cuff. Such a difference in pressure may increase the air flow from the inter-cuff chamber into the direction of the oropharynx.

In a particular embodiment, the present invention relates to a ventilation method according to the present invention, wherein pressurizing the inter-cuff chamber comprises allowing air to flow into said inter-cuff chamber, i.e. pressurizing by putting air pressure on the inter-cuff region. In a more particular embodiment, the air-pressure provided in the inter-cuff chamber is 5 cm $H_2O$.

According to a particular embodiment the present invention also relates to the use of a ventilation device according to the present invention for preventing pneumonia and more particularly Ventilator-associated pneumonia (VAP). The present invention also relates to the use of a ventilation device according to the present invention for ventilating patients diagnosed with pneumonia, and more particularly Ventilator-associated pneumonia. The use of the ventilation devices according to the present invention prevents leakage of proximal secretions through the cuffed region of the ventilation device, thereby avoiding that these secretions reach the airways and cause pneumonia. Also for patients diagnosed with pneumonia the ventilation devices according to the present invention is envisaged as the use of these ventilation devices will prevent further aggravation of the pneumonia or prevent secondary pneumonia caused by the leakage of proximal secretions to the airways.

According to a particular embodiment the present invention also relates to a method for ventilating a patient comprising the step of providing to a patient in need of ventilation, with a ventilation device according to the present invention. More particularly, the ventilation method comprises the step of inserting a ventilation device according to the present invention into the trachea of said patient and pressurizing the inter-cuff chamber formed thereby.

In yet another aspect, the present invention relates to a kit comprising a ventilation device according to the present invention or a ventilation system according to the present invention and instructions for use setting forth a method according to the present invention.

The present invention is illustrated by a number of figures of particular embodiments of the invention and which are not intended to limit the invention.

FIG. 1 illustrates a ventilation device 1 according to a particular embodiment of the present invention. The ventilation device 1 comprises ventilation tube 2 having a distal end 11 and a proximal end 10. The proximal end 10 is adapted to be connected to a conventional mechanical ventilation system (not illustrated). The ventilation tube 2 is provided with a primary cuff 4 and a secondary cuff 6. The inter-cuff region of the ventilation tube is provided with an internal port 9 of the pressurization lumen which is used to discharge gas into the inter-cuff chamber formed upon placement of the device into the trachea, to provide a positive pressure thereto.

At the proximal end of the lumens of the ventilation device external pneumatic valves or connection elements are provided. Two pneumatic valves 22 and 23 are connected to the cuff inflation lumens 25 and 26, while the pressurization lumen 24 is provided with a connection element 21.

Figure 2:
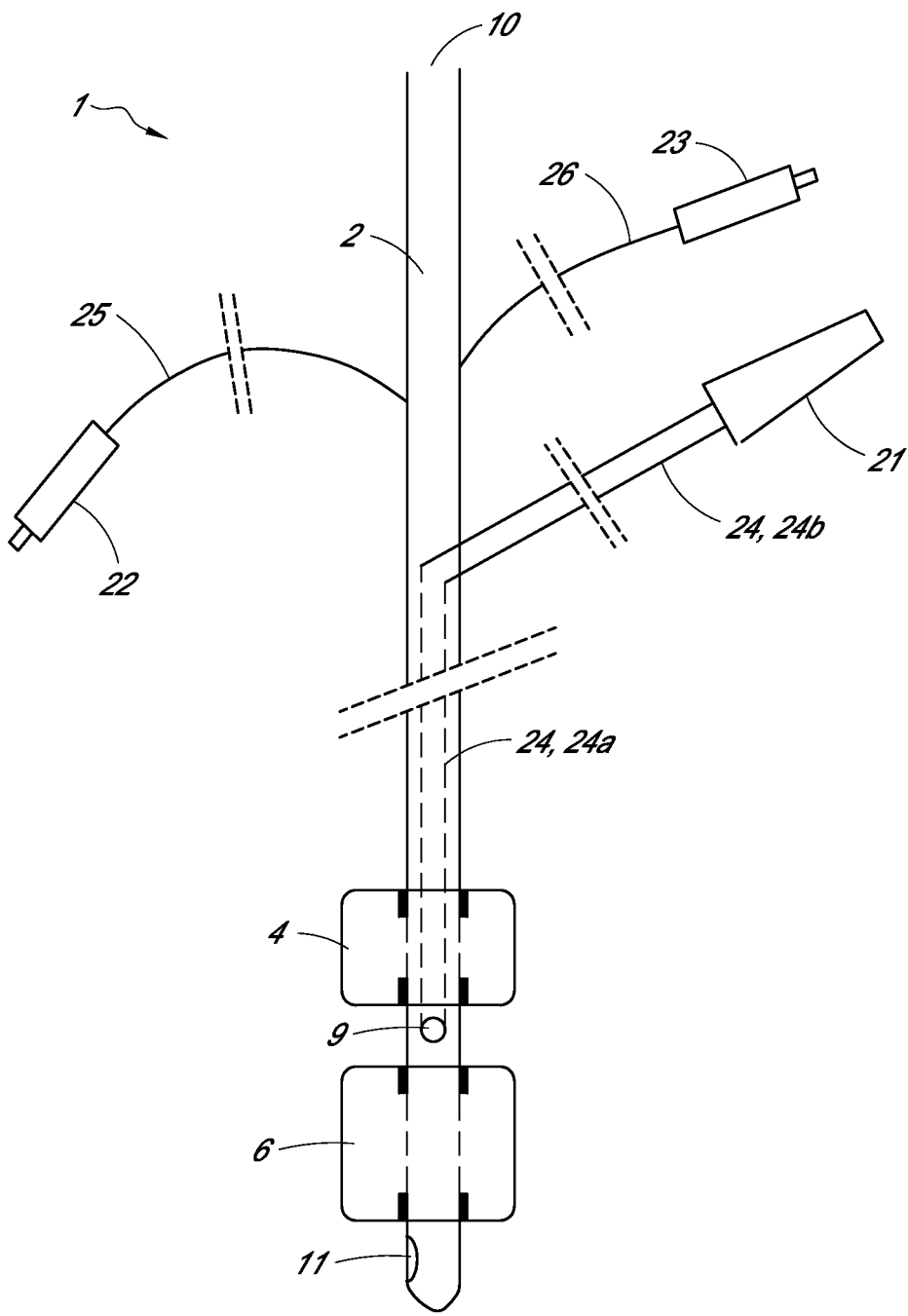
FIG. 2 illustrates an exemplary embodiment of a ventilation device according to a particular embodiment of the invention.

FIG. 2 represents a ventilation device 1 according to a particular embodiment of the present invention. The ventilation device 1 comprises ventilation tube 2 having a distal end 11 and a proximal end 10. The ventilation tube 2 is provided with a primary cuff 4 and a secondary cuff 6. The inter-cuff region of the ventilation tube is provided with an internal port 9 of the pressurization lumen 24 which is used to discharge gas into the inter-cuff chamber formed upon placement of the device into the trachea, to provide a positive pressure thereto. One part 24a (dashed line) of the pressurization lumen 24 is positioned inside the ventilation tube, preferably in the tube wall, whereas another part 24b of the pressurization lumen 24 is located outside the ventilation tube. Preferably part 24b has a larger internal diameter than part 24a. The pressurization lumen 24 is further provided with a connection element 21 for connection to a pressure regulator (not shown).

Figure 3:
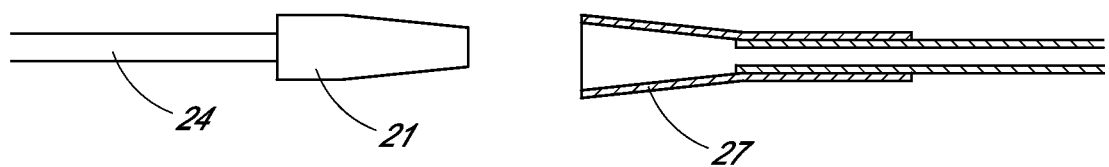
FIG. 3 illustrates an exemplary embodiment of a connection element on the external port of a pressurization lumen according to a particular embodiment of the invention.

FIG. 3 illustrates an exemplary embodiment of a connection element 21 on the external port of a pressurization lumen 24 according to a particular embodiment of the invention. The shape of the connection element 21 matches with the shape of a connection element 27 provided on a pressure regulator. Thus the connection element 21 ensures the connection of the pressurization lumen to a pressure regulator.

Figure 4:
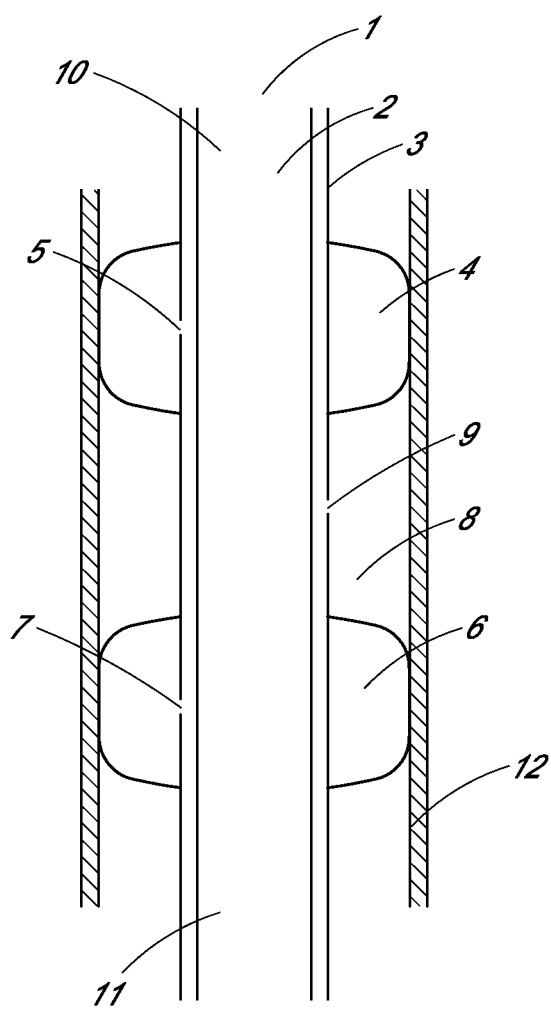
FIG. 4 illustrates an exemplary embodiment of a ventilation device according to a particular embodiment of the invention.

FIG. 4 describes a schematic representation of detail of a ventilation device 1 as placed in the trachea of a patient according to a particular embodiment of the present invention. The ventilation device 1 comprises ventilation tube 2 having a distal end 11 and a proximal end 10. The distal end 11 is positioned in the trachea of a patient to deliver air in order to mechanically ventilate the patient (and optionally deliver anesthetics or other bioactive agents) in a conventional manner. The ventilation device is further provided with a primary cuff 4 which may be inflated from a collapsed or low profile configuration to an expanded or inflated configuration using a cuff inflation port 5 and a secondary cuff 6 which may be inflated from a collapsed or low profile configuration to an expanded or inflated configuration using a cuff inflation port 7. An inter-cuff chamber 8 is formed by the primary cuff, the secondary cuff, the inter-cuff region of the ventilation tube and the trachea wall 12. Said inter-cuff region is provided with an internal port 9 of a pressurization lumen 3 which is used to discharge gas into the inter-cuff chamber 8 to provide a positive pressure.

Figure 5:
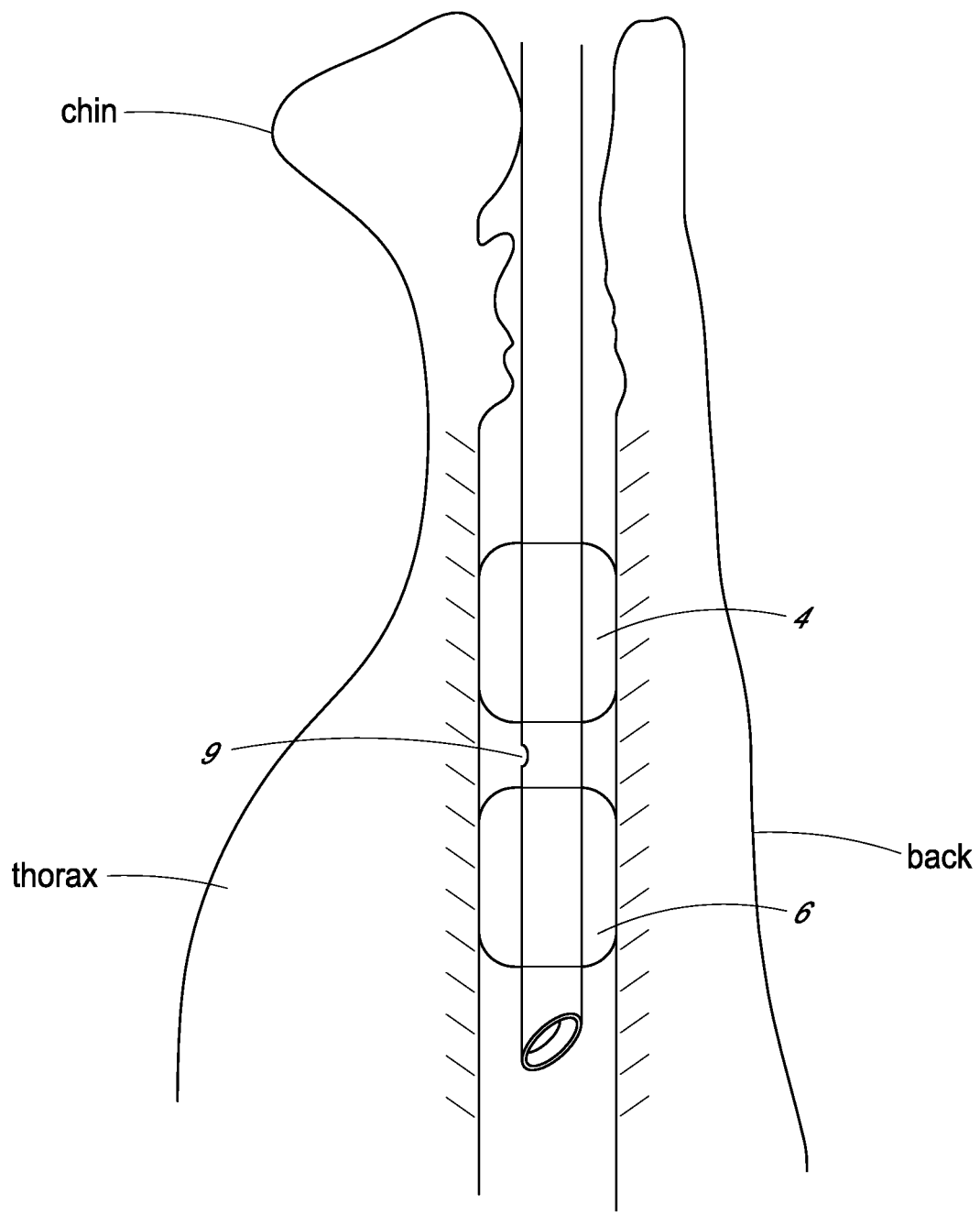
FIG. 5 illustrates the position of an exemplary embodiment of a ventilation device according to a particular embodiment of the invention in the trachea of a patient.

FIG. 5 shows the position of a ventilation device 1 according to a particular embodiment of the present invention in the trachea of a patient.

In order to better explain the characteristics of the invention, the following provides examples of the use of a device according to a particular embodiment of the invention, which is provided to illustrate the advantages of the invention without intending to be limitative in any way.

EXAMPLES a) Comparative Test

The present example describes experiments wherein the ability to prevent proximal fluid leakage of a ventilation tube according to the present invention is compared to 3 commercialized single-cuffed ventilation tubes.

An artificial trachea with jagged inside walls and an internal diameter of 23 mm was used to mimick the in vivo situation. The jagged walls of the artificial trachea closely resemble the real trachea surface and therefore provide more realistic experimental conditions than the glass tubes with smooth inside walls often used in testing such devices. A ventilation tube according to the present invention was compared to 3 commercialized single-cuffed ventilation tubes no 8: the polyvinyl cuff (classical) Portex®, the polyvinyl cuff (pear-formed) TaperGuard Evac® Mallinckrodt and the polyurethane Microcuff® Kimberly-Clark. The ventilation tubes were positioned in the artificial trachea and 3.4 ml of a methylene blue solution was administered above the cuffs. Different cuff pressures were applied and kept constant by a continuous cuff pressure control device. The inflow of the methylene blue solution below the cuffs was monitored. Inter-cuff chamber pressure was always kept at 5 cm $H_2O$. All experiments lasted 120 minutes.

At a cuff pressure of 15 cm $H_2O$, after 120 minutes an inflow of full content of the methylene blue solution was observed in all three commercialized tubes. No inflow of the methylene blue solution beyond the cuffs was observed for the ventilation tube according to the present invention.

At a cuff pressure 20 cm H$_2$O, after 120 min an inflow of full content of the methylene blue solution was observed in all three commercialized tubes. No inflow of the methylene blue solution beyond the cuffs was observed for the ventilation tube according to the present invention.

At a cuff pressure 30 cm H$_2$O, after 120 min an inflow of full content of the methylene blue solution was observed in all three commercialized tubes. No inflow of the methylene blue solution beyond the cuffs was observed for the ventilation tube according to the present invention.

The same experiment as described above was performed using the inside of a syringe instead of a model of an artificial trachea. At a cuff pressure 30 cm H$_2$O after 120 min an inflow of full content of the methylene blue solution was observed for the Portex ventilation tube. No inflow was observed for the other ventilation tubes.

From these experiments it can be concluded that the ventilation tube according to the present invention prevents the leakage of proximal secretions through the cuff region, thereby avoiding that these secretions reach the airways. Even at very low cuff pressure (15 cm H$_2$O) no leakage occurs, which indicates that the ventilation tube according to the present invention still prevents leakage in case of an acute cuff deflation (e.g. accidental disconnection) or chronic cuff deflation (e.g. progressive loss of cuff pressure which generally occurs over time in all ventilated patients). Furthermore, this indicates that the ventilation tubes according to the present invention do not require high cuff inflating pressures, thus reducing the risk of tracheal trauma and late stricture lesions.

b) Comparative Test During and after Ventilation

The present example describes experiments wherein the ability to prevent proximal fluid leakage during mechanical ventilation was tested. In these experiments, the ventilation tube according to the present invention is compared to commercialized polyurethane Microcuff® Kimberly-Clark tubes, which are considered to be providing the best sealing capacity (Pitts R et al., Intensive Care Medicine 2010, 36, 2066-2073).

An artificial trachea with an internal diameter of 23 mm was used to mimick the in vivo situation. A prototype of the ventilation tube according to the present invention was compared to commercialized polyurethane (PU) Microcuff® Kimberly-Clark single-cuffed ventilation tubes (no 8). On the commercialized PU tubes, cuff pressures of 20 and 30 cmH$_2$O were applied and kept constant by a continuous cuff pressure control device. On the prototype tubes according to the present invention, a cuff pressure of 20 cmH$_2$O was applied to the proximal cuff and a pressure of 30 cmH$_2$O was applied to the distal cuff. The cuffs of the prototype tube were made of polyvinyl chloride (PVC). Inter-cuff chamber pressure was always kept at 5 cmH$_2$O.

The ventilation tubes were positioned in the artificial trachea and 3.4 ml of a methylene blue solution was administered above the cuffs, corresponding to a fluid column of 1 cm. The inflow of the methylene blue solution below the cuffs was monitored. Ventilation was obtained using a pressure-controlled Dräger XL ventilator. A PEEP of 5 cmH$_2$O, a tidal volume around 500 mL, a frequency of 15/min and a I:E ratio (ratio of the duration of inspiration to the duration of expiration) of 1:2 was applied.

Five experiments were performed at random times. For each experiment, a new tube was used. The results of these experiments are summarized in Table 1 and show that both the prototype PVC-cuffed and the commercial PU-cuffed tubes provide adequate and complete sealing, as no fluid leakage beyond the (proximal) cuff was observed. The results further show that both the prototype PVC and commercialized PU tubes do not influence the tidal volume, which remained constant during the experiments. However, in contrast with the commercialized tubes, the prototype offers the benefit that it allows significant retrograde flow of secretions towards the oropharynx.

TABLE 1

Experimental results during ventilation

| Parameter | Prototype PVC 20/30 cmH$_2$O | PU 20 cmH$_2$O | PU 30 cmH$_2$O |
|---|---|---|---|
| Fluid leakage alongside the cuff (visual) | Up to midst of proximal cuff length | Up to upper third of cuff length | Up to upper third of cuff length |
| Fluid leakage beyond the cuff | none | none | None |
| Height of retrograde (= directed to oropharynx) fluid column (cm) | 5.6 ± 1.4 | 0 (episodic burst of bubbles) | 0 (few air bubbles) |
| Tidal volume during 8 h of ventilation (mL ± standard deviation) | 475 ± 15 | 485 ± 18 | 476 ± 16 |

Also the effects of disconnection of the ventilator from the tube were compared. Table 2 shows the results of experiments wherein the ventilator was disconnected from the tubes after eight hours of ventilation. Disconnection of the ventilator results in an acute disappearance of positive inspiratory and expiratory (PEEP) pressure. With the commercialized PU tubes, disconnection of the ventilator results in leakage through the cuff after a few minutes. The leakage depends on the cuff pressure and is generally two to three times higher at a cuff pressure of 20 cmH$_2$O than at 30 cmH$_2$O. However, no leakage was observed with the prototype tubes according to the present invention, due to the positive inter-cuff pressure.

TABLE 2

Experimental results after disconnection from the ventilator

| Parameter | Prototype PVC 20/30 cmH$_2$O | PU 20 cmH$_2$O | PU 30 cmH$_2$O |
|---|---|---|---|
| Time after which leakage starts | No leakage | 55-120 s | 105-360 s |
| Leakage volume after 10' (range) | 0 | 0.5-3 mL | 0.2-0.7 mL |
| Leakage flow | 0 | 0.2 mL/min | 0.06 mL/min |

What is claimed is:

1. A method for ventilating a patient comprising:
providing a ventilation device for mechanical ventilation suitable to be partly positioned inside the trachea of a patient, comprising:
a single ventilation tube with a single ventilation lumen, said ventilation tube having a proximal end and a distal end;
only two cuffs comprising a primary cuff and a secondary cuff in distal position with respect to said primary cuff, said primary and secondary cuffs being provided with one or more cuff inflation lumens, suitable to inflate and/or deflate said primary and/or secondary cuffs; and;
an inter-cuff region separating said primary cuff and said secondary cuff;

wherein said ventilation device further comprises a pressurization lumen for pneumatically pressurizing said inter-cuff region, said pressurization lumen having an external port near the proximal end of said ventilation tube and at least one internal port positioned between said primary and secondary cuff, said at least one internal port being a gas discharge port discharging gas into an inter-cuff chamber formed by the trachea wall, the inter-cuff region and the primary and secondary cuffs;

inserting said ventilation device orally into a patient, wherein both the primary cuff and the secondary cuff are placed into the trachea of the patient, and said single ventilation tube allows ventilation to both lungs simultaneously through said single ventilation lumen and said distal end of said ventilation tube;

while maintaining said primary and secondary cuff in the trachea, inflating said primary and secondary cuff thereby forming an inter-cuff chamber formed by the trachea wall, the inter-cuff region and the primary and secondary cuffs;

pneumatically pressurizing the inter-cuff chamber such that pressure inside said inter-cuff chamber is larger than pressure proximal from said primary cuff;

delivering oxygen to said patient through said ventilation tube.

2. The method according to claim 1, wherein pressurizing the inter-cuff chamber comprises allowing air to flow into said inter-cuff chamber.

3. A ventilation system comprising:
(a) a ventilation device for mechanical ventilation suitable to be partly positioned inside the trachea of a patient, comprising:
    a single ventilation tube with a single ventilation lumen, said ventilation tube having a proximal end and a distal end, said single ventilation tube allowing ventilation to both lungs simultaneously through said single ventilation lumen and said distal end;
    only two cuffs comprising a primary cuff and a secondary cuff in distal position with respect to said primary cuff, said primary and secondary cuffs being provided with one or more cuff inflation lumens, suitable to inflate and/or deflate said primary and/or secondary cuffs; and;
    an inter-cuff region separating said primary cuff and said secondary cuff such that upon insertion into the trachea and inflation of said primary and secondary cuff an inter-cuff chamber is formed by the trachea wall, the inter-cuff region and the primary and secondary cuffs;
    wherein said ventilation device additionally comprises a pressurization lumen for pneumatically pressurizing said inter-cuff region, said pressurization lumen having an external port near the proximal end of said single ventilation tube and at least one internal port positioned between said primary and secondary cuff, said at least one internal port being a gas discharge port discharging gas into an inter-cuff chamber formed by the trachea wall, the inter-cuff region and the primary and secondary cuffs;
(b) a ventilation source connected to said proximal end of said single ventilation tube;
(c) an inflation device suitable for selectively inflating and/or deflating said primary and secondary cuffs, said inflation device being connected to said one or more cuff inflation lumens; and
(d) a pressure regulator connected to said pressurization lumen which monitors and adapts the pressure in said inter-cuff region by selectively pressurizing and depressurizing said inter-cuff region between said primary and said secondary cuffs in order to avoid leakage of secretions alongside the primary cuff.

4. The ventilation system according to claim 3 wherein said primary and secondary cuff are each provided with a dedicated cuff inflation lumen.

5. The ventilation system according to claim 3 wherein said external port of said pressurization lumen is provided with a connection element for connection to said pressure regulator.

6. The ventilation system according to claim 3 comprising at least three internal ports being gas discharge ports discharging gas into the inter-cuff chamber formed by the trachea wall, the inter-cuff region, and the primary and secondary cuffs; said at least three internal ports being positioned symmetrically along a single circumferential sector of said tube.

7. The ventilation system according to claim 3 wherein said primary cuff has a length in axial direction of said ventilation tube which is shorter than the length of said secondary cuff.

8. The ventilation system according to claim 3 wherein said ventilation device is further provided with one or more aspirating and/or irrigating lumens.

9. The ventilation system according to claim 3 wherein said primary and said secondary cuff are axially spaced apart by a distance in the range from 0.5 cm to 3 cm.

10. The ventilation system according to claim 3 wherein said ventilation device further comprises a distal lumen having an external port near the proximal end of said ventilation tube and an internal port near the distal end of said ventilation tube, said distal lumen being suitable to allow inoculation of substances directly into the respiratory system of the patient.

11. The ventilation system according to claim 3 wherein said ventilation device is an endotracheal or tracheostomy device.

12. The ventilation system according to claim 3 wherein said pressure regulator controls delivery air to said inter-cuff region.

13. The ventilation system according to claim 3 wherein said pressure regulator operates on a continuous basis.

14. A ventilation device for mechanical ventilation suitable to be partly positioned inside the trachea of a patient, comprising:
    only one ventilation tube with a single ventilation lumen, said ventilation tube having a proximal end and a distal end, said single ventilation tube allowing ventilation to both lungs simultaneously through said single ventilation lumen and said distal end;
    only two cuffs comprising a primary cuff and a secondary cuff in distal position with respect to said primary cuff, said primary and secondary cuffs being provided with one or more cuff inflation lumens, suitable to inflate and/or deflate said primary and/or secondary cuffs; and
    an inter-cuff region separating said primary cuff and said secondary cuff;
wherein said ventilation device additionally comprises a pressurization lumen for pneumatically pressurizing said inter-cuff region, said pressurization lumen having an external port near the proximal end of said one ventilation tube and at least one internal port positioned between said primary and secondary cuff, said at least one internal port being a gas discharge port discharging gas into an inter-cuff chamber formed by the trachea wall, the inter-cuff region, and the primary and secondary cuffs;

a pressure regulator connected to said pressurization lumen which monitors and adapts the pressure in said inter-cuff region by selectively pressurizing and depressurizing said inter-cuff region between said primary and said secondary cuffs in order to avoid leakage of secretions alongside the primary cuff.

* * * * *